United States Patent
Lovett et al.

(10) Patent No.: US 6,501,987 B1
(45) Date of Patent: Dec. 31, 2002

(54) RATE SMOOTHING CONTROL

(75) Inventors: Eric G. Lovett, Roseville, MN (US); Surekha Palreddy, Vadnais Heights, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 0 days.

(21) Appl. No.: 09/579,951

(22) Filed: May 26, 2000

(51) Int. Cl.[7] .............................................. A61N 1/365
(52) U.S. Cl. ............................................. 607/9; 607/17
(58) Field of Search .............................. 600/515, 519, 600/521, 508, 509, 520, 522, 523; 607/9, 14, 15, 17, 25, 19, 20

(56) References Cited

U.S. PATENT DOCUMENTS

| | | | |
|---|---|---|---|
| 4,163,451 A | 8/1979 | Lesnick et al. | 128/419 PG |
| 4,503,857 A | 3/1985 | Boute et al. | 128/419 PG |
| 4,562,841 A | 1/1986 | Brockway et al. | |
| 4,830,006 A | 5/1989 | Haluska et al. | 607/4 |
| 4,944,298 A | 7/1990 | Sholder | 128/419 PG |
| 5,085,215 A | 2/1992 | Nappholz et al. | 128/419 PG |
| 5,144,949 A | 9/1992 | Olson | 128/419 PG |
| 5,156,147 A | 10/1992 | Warren et al. | 128/419 PG |
| 5,197,467 A * | 3/1993 | Steinhaus et al. | 607/20 |
| 5,292,339 A | 3/1994 | Stephens et al. | 607/15 |
| 5,480,413 A | 1/1996 | Greenhut et al. | 607/14 |
| 5,549,649 A | 8/1996 | Florio et al. | |
| 5,584,867 A | 12/1996 | Limousin et al. | 607/9 |
| 5,725,561 A * | 3/1998 | Stroebel et al. | 607/9 |

OTHER PUBLICATIONS

Heuer, H., et al., "Dynamische Zweikammer–Overdrive–Stimulation mit einem implantierbaren Schrittmachersystem als neue Methode zur Beendigung Langsamer ventrikularer Tachykardien", *Z Kardiol*; 75, (1986), pp. 673–675.

"Pacemaker System Guide for PULSAR MAX II; Multi-programmable Pacemakers", Product brochure published by Guidant Corporation, pp. 6–48 and 6–49, (Apr. 18, 1999).

"Pacemaker System Guide for PULSAR MAX II; Multi-programmable Pacemakers", Product brochure published by Guidant Corporation, p. 6–39, (1999).

"Vitatron Harmony Automatic Dual Chamber Pacemaker Product Information and Programmable Guide", Product Brochure published by Vitatron Medical, 22 pgs, (Date Unknown) before Sep. 11, 1991.

Blommaert, D., et al., "Effective Prevention of Atrial Fibrillation by Continuous Atrial Overdrive Pacing After Coronary Artery Bypass Surgery", *JACC*, vol. 35, No. 6, pp. 1411–1415, (May 2000).

Campbell, R.M., et al., "Atrial Overdrive Pacing for Conversion of Atrial Flutter in Children", *Pediatrics*, vol. 75, No. 4, pp. 730–736, (Apr. 1985).

Garrigue, S., et al., "Prevention of Atrial Arrhythmias during DDD Pacing by Atrial Overdrive", *PACE*, vol. 21, pp. 1751–1759, (Sep. 1998).

Murgatroyd, F.D., et al., "A New Pacing Algorithm for Overdrive Suppression of Atrial Fibrillation", *Pace*, vol. 17., pp. 1966–1973, (Nov. 1994, Part II).

(List continued on next page.)

Primary Examiner—George R. Evanisko
(74) Attorney, Agent, or Firm—Schwegman, Lundberg, Woessner & Kluth, P.A.

(57) ABSTRACT

A rate smoothing function used in implantable pulse generators, where detected triggering events cause the rate smoothing function to be activated or deactivated and detected parameter adjusting events cause parameters of the rate smoothing function to be changed. The activation/deactivation and/or change to the parameters of the rate smoothing function are temporary, and the pre-event state of the rate smoothing function is set to a post-adjusting state. In one embodiment, the pre-event state of the rate smoothing function is set to the post-adjusting state after a first time interval.

19 Claims, 5 Drawing Sheets

OTHER PUBLICATIONS

Sutton, R., "Pacing in Atrial Arrhythmias", *PACE*, vol. 13, pp. 1823–1827, (Dec. 1990, Part II).

Zhu, D.W., et al., "Electrophysiology, Pacing and Arrythmia", *Clin. Cardiol.*, vol. 19, pp. 737–742, (Sep. 1996).

"Vitatron Harmony Automatic Dual Chamber Pacemaker Product Information and Programming Guide", Product Brochure published by Vitatron Medical, 22 pgs, (Date Unknown).

"French CNH Equipment Approvals", *Clinica*, 417, p. 9, 3 pages, (Sep. 5, 1990).

"Rate–Adaptive Devices Impact Pacemaker Market", *Clinica*, 467, p. 16, 6 pages, (Sep. 11, 1991).

Fromer, M., et al., "Algorithm for the Prevention of Ventricular Tachycardia Onset: The Prevent Study", *The American Journal of Cardiology*, 83 (5B), pp. 45D–47D, (Mar. 11, 1999).

* cited by examiner

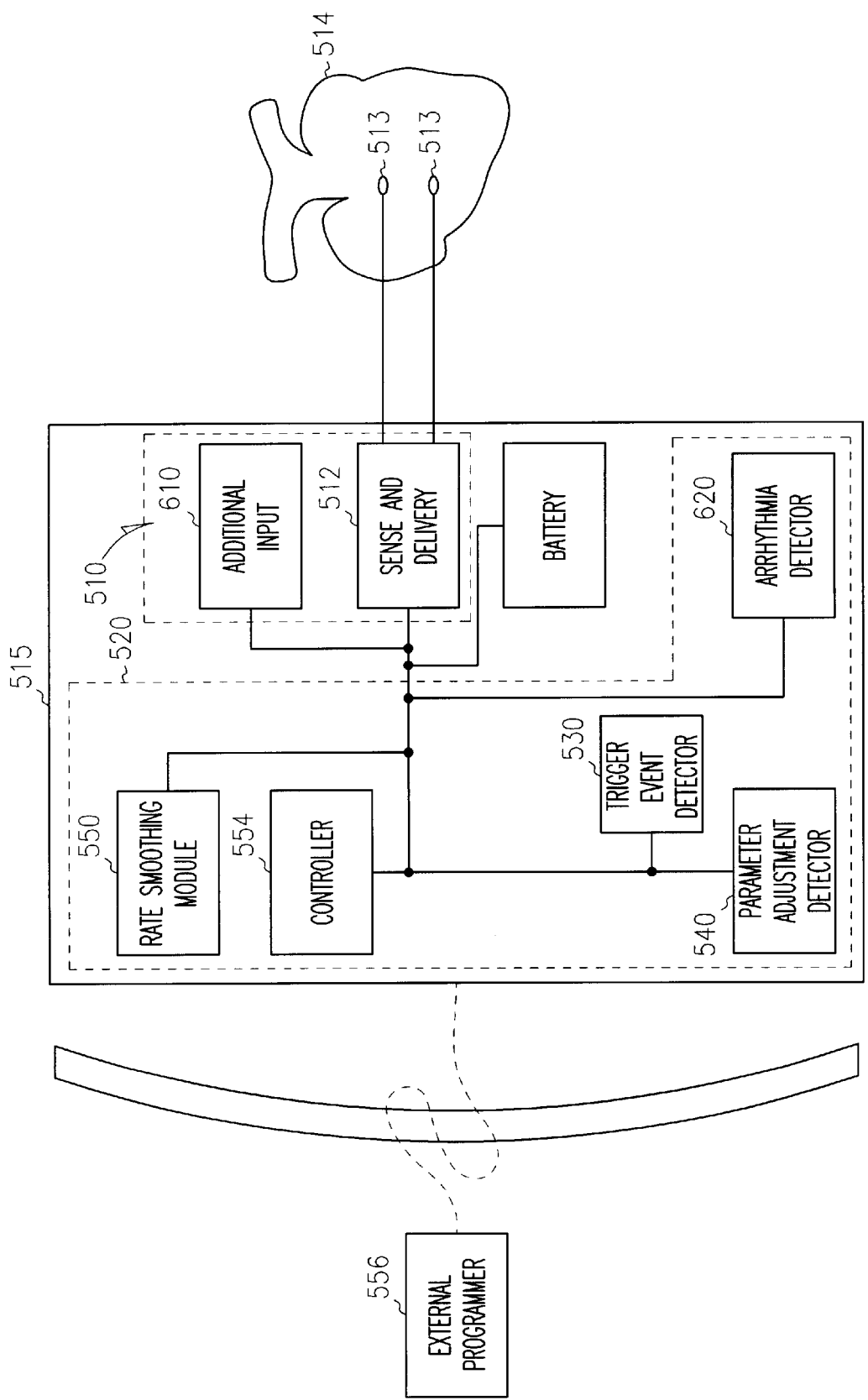

RATE SMOOTHING CONTROL

TECHNICAL FIELD

The present invention relates to pulse generators and in particular to implantable pulse generators that control pacing functions based on sensed events.

BACKGROUND

The cardiac pacemaker in its simplest form is an electrical circuit in which a battery provides electricity that travels through a conducting wire through the myocardium, stimulating the heart to beat ("capturing" the heart), and back to the battery, thus completing the circuit. Implantable cardiac pacemakers have been in existence since the later 1950's, although external pacemakers were known even earlier. Since that time great strides have been made in improving upon the leads and the pulse generators that together comprise the pacemaker. In particular, the pulse generator circuitry has evolved from discrete components to semi-custom integrated circuits, which are now fabricated from complimentary metal oxide semi-conductor (CMOS) technology.

As cardiac pacemakers have evolved they have been designed to provide increases in the heart rate for periods when the patient is experiencing physiological stress. These "rate-modulating" pacemakers help the patient adapt to physiological stress with an increase in heart rate, even if the patient's intrinsic heart rate would not allow this to occur. The development of dual-chamber pacemakers has allowed the patient to increase their heart rate if he or she is in sinus rhythm.

The rate-modulated pacemaker has three major components. The first is an indicator, such as for activity, body temperature, or respiratory rate, that provides an approximate measurement of metabolic needs. The second is a sensor that can measure the indicator chosen, such as measurement of body temperature or respiratory rate. The third is a rate controlled algorithm that is in the software of the pacemaker and modulates the pacemaker rate as the sensors send signals to the pacemaker.

As the sensors indicate greater metabolic need, the pacing rate is increased. The rate at which the pacing rate increases, however, is bounded and controlled by a feature called rate smoothing. Rate smoothing is a gradual slowing or speeding of the pacemaker rate based on a percentage of a preceding cardiac interval. This is a mechanism programmed into so types of pacemakers to reduce or to smooth abrupt changes in paced rate, especially at the upper rate limit of dual chamber pacemakers. Conversely, if a patient were to develop an ectopic atrial tachycardia, this programmed feature would cause gradual increase in rate rather than abrupt increase in rate.

Rate smoothing is, however, not always a desirable feature under certain circumstances. For example, when an individual needs rapid cardiac output in a short time, such as in a stressful situation, rate smoothing will prevent the heart rate from rising rapidly enough to keep-up with the individual's cardiac demands. Similarly, once the stressful situation has passed the individual's will slow only at the rate dictated by the rate smoothing algorithm. This situation can lead to unnecessary constraints on the heart rate. Also, the pacemaker provides pacing pulses that are unnecessary for the proper functioning of the heart (e.g., wastes battery resources on unnecessary pacing pulses). Thus, a need exists in the art to provide for a more flexible way of utilizing the rate smoothing algorithm.

SUMMARY

The present invention provides a system and method for controlling a rate smoothing system in a pulse generating system. In one embodiment, the rate smoothing system is either activated or deactivated (turned on or turned off) when a triggering event is detected. In an alternative embodiment, when a parameter adjusting events is detected parameters of the rate smoothing system are adjusted (e.g., changed). Under either situation (turning on/off or adjustment of parameters) the changes to the rate smoothing system/ function are temporary. In one embodiment, the duration of the changes is over a first time interval, after which the rate smoothing system is either set to the original pre-event state or to a state in which one or more of the original parameter values/settings have been changed from the original pre-event state. By allowing selected events to temporarily activate/deactivate or change parameter settings for a rate smoothing system, greater flexibility in treating a patient's cardiac conditions is achieved as compared to allowing the rate smoothing function to continuously operate. The present subject matter can be used with rate smoothing systems applied to either ventricular pacing or atrial pacing.

In one embodiment, the present system provides monitoring for a trigger signal a parameter adjusting event or both. In one embodiment, the system uses a signal input system, where the signal input system is adapted to detect a signal. Control circuitry coupled to the signal input system receives the signal from the signal input system. In one embodiment, a trigger event detector in the control circuitry receives the signal and analyzes the signal for the occurrence of the trigger event. The trigger event detector is further coupled to a rate smoothing module. In one embodiment, the rate smoothing module executes and controls the rate smoothing algorithm. When the triggering event is detected, the rate smoothing module is then either activated to provide rate smoothing or deactivated to stop rate smoothing, depending upon the state of the module prior to the triggering event. Once the rate smoothing system is activated or deactivated, a timer is used to time a first interval. After the first interval expires, the rate smoothing system is then reset, or restored, to its state prior to the trigger signal. Alternatively, after the first interval expires, the rate smoothing system changes one or more of the original parameter values/settings (i.e., pre-trigger signal parameter state or pre-parameter adjusting event parameter state) to provide a new parameter state. The new parameter state is then used in the rate smoothing system until a subsequent trigger signal and/or parameters adjusting event is detected. A new parameter state can be created after each trigger signal and/or parameters adjusting event (e.g., a sequence of changes to the parameter values and/or settings for the rate smoothing system).

In an alternative embodiment, a parameter adjustment event detector coupled to the control circuity receives the signal from the signal input system. In one embodiment, the parameter adjustment event detector receives and signal and analyzes the signal for the occurrence of a parameter adjustment event in the signal. When the parameter adjustment event is detected, the rate smoothing module adjusts rate smoothing parameters. In one embodiment, the parameters adjusted are the percent change in pacing rate for either up or down rate smoothing.

Any number of detected events are used as either triggering events or parameter adjustment events. For example, triggering events or parameter adjustment events are detected in activity signal sensed using activity monitors such as accelerometers or minute ventilation systems. In this embodiment, an activity signal is monitored from an activity sensor. The triggering event or parameter adjustment event is then detected when the activity signal exceeds a first predetermined value. In an additional embodiment, the activity signal is a heart rate acceleration, where the triggering event or parameter adjustment event is when a heart rate trajectory exceeds the first predetermined value.

In an additional embodiment, triggering events or parameter adjustment events are found in monitored cardiac signals. For example, monitoring for the triggering event or parameter adjustment events includes monitoring a cardiac signal which includes indications of ventricular contractions. The cardiac signal is then analyzed for the occurrence of premature ventricular contractions (PVC). When one or more PVC occur, the triggering event or parameter adjustment event is detected. Alternatively, the cycle length pattern of cardiac cycles detected in the cardiac signal are used as triggering events or parameter adjustment events. For example, a detected short-long-short cycle length sequence from a cardiac signal is a triggering event or parameter adjustment event. Alternatively, the triggering event or parameter adjustment event is when a cardiac rate exceeds a rate threshold. In an additional embodiment, the triggering event or parameter adjustment event occurs after the end of an arrhythmic episode.

In an alternative embodiment, triggering events or parameter adjustment events occur at selected times within a time interval. For example, monitoring for the triggering event or parameter adjustment events includes monitoring a time interval, such as the time of the day, week, month, year or event the season of the year. The triggering event or parameter adjustment event is then detected at a first time in the time interval, where the first time is either programmed by the physician or set based on the implantable systems analysis of one or more detected signals. Alternatively, the triggering event or parameter adjustment event is when a pacemaker mode is changed.

BRIEF DESCRIPTION OF THE DRAWINGS

FIG. 6 is a block diagram of one embodiment of an implantable medical device according to the present subject matter.

DETAILED DESCRIPTION

In the following detailed description, references are made to the accompanying drawings that illustrate specific embodiments in which the invention may be practiced. Electrical, mechanical, programmatic and structural changes may be made. to the embodiments without departing from the spirit and scope of the present invention. The following detailed description is, therefore, not to be taken in a limiting sense and the scope of the present invention is defined by the appended claims and their equivalents.

Rate smoothing provides a measure of control over the rate of change of the ventricular pacing rate. Specifically, the rate of change of the ventricular pacing rate is controlled on a cycle-to-cycle basis so as to maintain the rate of change within a programmed percentage of the previous cycle's rate. This function is achieved via the comparison of the ventricular pacing rate for each cycle to a "rate window" or percentage of the period for the previous cardiac cycle so as to ensure that the period of the pacing pulses is constrained from cycle to cycle by the limits defined by the rate window.

Controlling when and under what cardiac conditions to turn on/off or adjust the parameters for a rate smoothing program is highly advantageous. This control allows the rate smoothing to be deactivated when use of rate smoothing would be detrimental, or constraining, to a patient's need for rapid heart rate acceleration or deceleration. Furthermore, by selectively turning rate smoothing off or adjusting rate smoothing parameters, the number of pacing pulses delivered to a patient is reduced.

Figure 1:
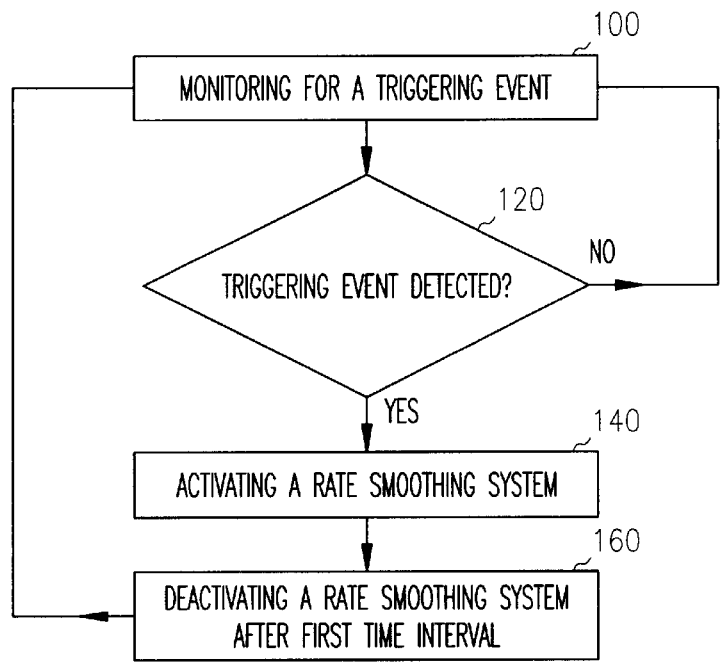
FIG. 1 shows one embodiment of a method according to the present invention.

FIG. 1 shows one embodiment of a method according to the present invention. At 100 a signal is sensed and analyzed for a triggering event. In one embodiment, the triggering event is any number of events sensed in either an activity signal coming from activity sensors (e.g., accelerometers, minute ventilation system, cardiac rate sensors) or a cardiac signal sensed from the patient's heart. In one embodiment, cardiac signals include either cardiac signals sensed from a ventricular location, or cardiac signals sensed from an atrial location.

At 120, the signal is then analyzed to detect the triggering event. When a triggering event is not detected, the signal continues to be analyzed. When a triggering event is detected, the rate smoothing system is activated at 140. Rate smoothing is then applied to control the changes in pacing rate as previously described. The rate smoothing is then deactivated at 160 at a time after activating the rate smoothing. In one embodiment, the time after activating the rate smoothing is a first time interval, where the first time interval is a programmable value. In an additional embodiment, the duration of the first time interval can also be changed based on information contained within either the activity or cardiac signals. Alternatively, the rate smoothing is deactivated based on information in the sensed activity signals or the cardiac signals, where the rate smoothing is deactivated when the one or more triggering events in the signals are no longer detected. Once the rate smoothing is deactivated, the system then returns to 100 to continue to monitor the signal for a triggering event.

Figure 2:
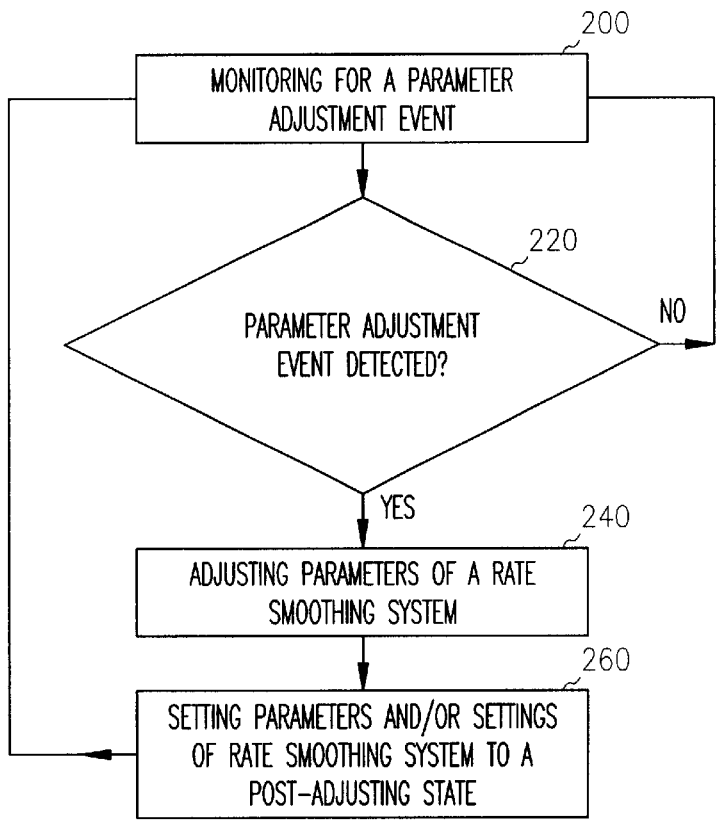
FIG. 2 shows one embodiment of a method according to the present invention.

FIG. 2 shows an additional embodiment of a method according to the present invention. At 200 a signal is sensed and analyzed for a parameter adjusting event. In one embodiment, the parameter adjusting event is any number of events sensed in the signal. For example, the signal can be an activity signal coming from activity sensors (e.g., accelerometers, minute ventilation system, cardiac rate sensors) or a cardiac signal sensed from the patient's heart. In one embodiment, cardiac signals include either cardiac signals sensed from a ventricular location, or cardiac signals sensed from an atrial location.

At 220, the signal is then analyzed to detect the parameter adjusting event. When a parameter adjusting event is not detected, the signal continues to be analyzed. When a parameter adjusting event is detected, parameters for the rate smoothing system are adjusted at 240. In one embodiment, adjusting the rate smoothing parameters includes making changes to parameter values for either up-smoothing or down-smoothing rate interval changes. For example, changes to the rate interval changes for down-smoothing can be made to set the rate interval in the range of six (6) to twelve (12) percent. Changes to the rate interval for up-smoothing can also be made to change the up-smoothing rate interval from, for example, 25 percent. Rate smoothing is then applied to control the changes in pacing rate as previously described. The parameters of the rate smoothing system are then set to a post-adjusting state at 260. In one embodiment, the post-adjusting state for the parameters and settings of the rate smoothing system includes restoring (i.e., resetting) the parameters and settings to their pre-parameter adjusting event state at a time after adjusting the parameters. Alternatively, adjusting the parameters of the rate smoothing system includes changing one or more of the original parameter values and/or settings (i.e., pre-trigger signal parameter state or pre-parameter adjusting event parameter state) to new parameters values and/or settings in a new parameter state. The new parameter state is then used in the rate smoothing system until a subsequent trigger signal and/or parameters adjusting event is detected. New parameter states can be created after each trigger signal and/or parameters adjusting event (e.g., a sequence of changes to the parameter values and/or settings for the rate smoothing system). This sequence of changes to the parameters values and/or settings also includes a change back to the original setting of the parameter values and/or settings of the rate smoothing system. In one embodiment, the changes to the parameter values and/or settings are based on information from sensed cardiac signals.

In one embodiment, the time after adjusting the parameters is a first time interval, where the first time interval is a programmable value. In an additional embodiment, the duration of the first time interval can also be changed based on information contained within either the activity or cardiac signals. Alternatively, the parameters of the rate smoothing are set to the post-adjusting state based on information in the sensed activity signals or the cardiac signals, where the rate smoothing parameters are set to the post-adjusting state when the one or more parameter adjusting events in the signals are no longer detected. Once the rate smoothing parameters are set to the post-adjusting state, the system then returns to 100 to continue to monitor the signal for a parameter adjusting event.

Figure 3:
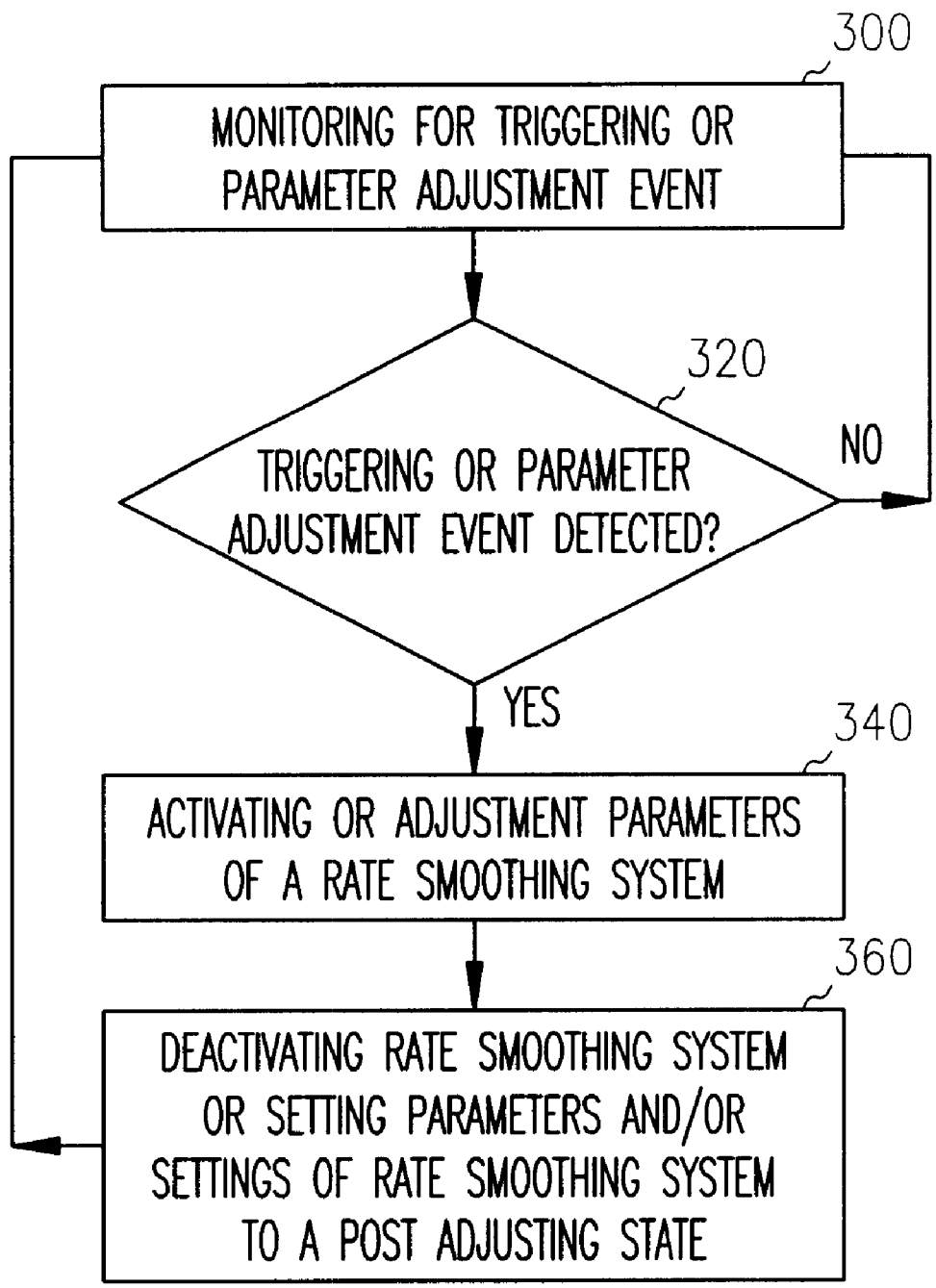
FIG. 3 shows one embodiment of a method according to the present invention.

FIG. 3 shows an addition embodiment of a method according to the present invention where a rate smoothing system can be controlled by both triggering events and parameters adjustment events. At 300 a signal is sensed and analyzed for a triggering event and/or parameter adjustment events, as previously described. At 320, the signal is then analyzed to detect either the triggering event or the parameter adjustment event. When a triggering event or a parameter adjustment event is not detected, the signal continues to be analyzed. When a triggering event or a parameter adjustment event is detected, however, the rate smoothing system is either activated (when a triggering event is detected) or parameters for the rate smoothing system are adjusted (when a parameter adjustment event is detected) at 340. With the present embodiment, it is possible that the rate smoothing is deactivated at 300, but is subsequently activated once a triggering event is detected. Once activated, sensed parameter adjustment events can cause the rate smoothing parameters to be adjusted.

At 360, the rate smoothing is either deactivated at a time after either activating the rate smoothing or the parameters of the rate smoothing system are set to the post-adjusting state as previously described at a time after adjusting the parameters, where the time for either deactivating or setting the parameters and/or states of the rate smoothing system at the post-adjusting state are as previously described. Once the rate smoothing has either been deactivated or set to the post-adjusting state, the system then returns to 300 to continue to monitor the signal for the triggering event and/or the parameter adjusting event.

As previously discussed, there exits a variety of triggering and parameter adjusting events. In one embodiment, triggering events or parameter adjustment events are detected in one or more activity signals sensed using activity monitors. Examples of activity monitors include accelerometers, minute ventilation systems or cardiac rate analyzer. In one embodiment, an activity signal is monitored from at least one of the activity monitors. The activity signal is analyzed to determine whether the activity signal has exceeded a first predetermined value. The triggering event and/or a parameter adjusting event are then detected when the activity signal exceeds the first predetermined value.

Examples of activity signals include a heart rate trajectory (heart rate vs. time) where the event is determined from the slope of the trajectory. Alternatively, the parameter adjusting event and/or the triggering event is detected when the cardiac rate exceeds a rate threshold. In an additional embodiment, the activity signal is an accelerometer signal from an accelerometer. In this embodiment, the amplitude (indication of motion) of the activity signal is analyzed to determine when the first predetermined value has been exceeded. In an alternative embodiment, the activity signal is a minute ventilation signal, where both the amplitude (depth of breath) and the frequency (breathing rate) of the signal are analyzed to determine if either has a value that exceed the first predetermined value. In one embodiment, the first predetermined value is based on the type of activity sensor being utilized and the portion of the signal that is being analyzed. Programmed values for the first predetermined value will also depend upon the patient's cardiac condition and the type of implantable system that is used to treat the patient. Thus, values for the different applications of the first predetermined value need to be set on a patient-by-patient basis.

In an additional embodiment, triggering events or parameter adjustment events are found in monitored cardiac signals. For example, monitoring for the triggering event or parameter adjustment events includes monitoring a cardiac signal which includes indications of ventricular contractions or atrial contractions. When ventricular contractions are detected, the cardiac signal is analyzed for the occurrence of premature ventricular contractions (PVC). In one embodiment, PVCs are identified based on a comparison of contraction intervals, where PVCs have a shorter interval relative to preceding intervals. In addition, PVCs are also identified based on an analysis of the morphology of the complex wave form (e.g., the QRS-complex wave form), in addition to a contraction interval analysis. When one or more PVC occur, the triggering event or parameter adjustment event is detected.

Figure 4:
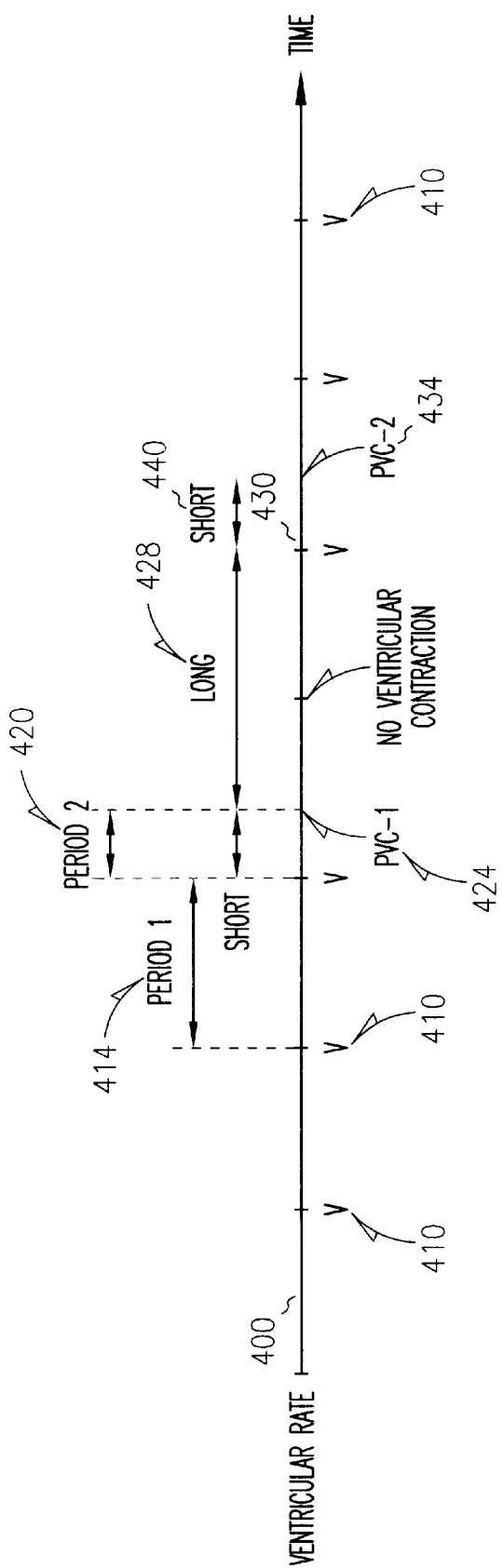
FIG. 4 shows an exemplary waveforms illustrating a triggering event/parameter adjusting event for the present subject matter.

Alternatively, the cycle length pattern of cardiac cycles detected in the cardiac signal are used as triggering events or parameter adjustment events. For example, a detected short-long-short cycle length sequence from a cardiac signal is a triggering event or parameter adjustment event. FIG. 4 shows one embodiment of a cardiac signal with cardiac intervals having a short-long-short cycle length sequence. In one embodiment, the cardiac signal is a ventricular signal 400 having indications of ventricular contractions 410. The ventricular contractions 410 define cardiac intervals, where a first cardiac interval is shown at 414. A second cardiac interval 420 is shown occurring after the first cardiac interval 410. The second cardiac interval 420 is, however, shorter than the first cardiac interval 410. In one embodiment, the second cardiac interval 420 is shorter due to a PVC 424. If a rate smoothing function were operating as this ventricular signal is sensed, the change in the pacing rate would be based off of either the first cardiac interval 410 or the second cardiac interval 420.

After the second cardiac interval 420, there is a long interval 428. In one embodiment, the long interval 428 is not interrupted by a ventricular pacing pulse as the myocardium are not in the proper state to be captured by the pulse. Ventricular pace 430, however, captures the ventricles, where the ventricular pace 430 is followed by another PVC 434 which results in a second short interval 440. Once this pattern of short-long-short cardiac intervals is presented the triggering event or the parameter adjustment event is detected. The rate smoothing function is then either turned on, or the parameters of the operating rate smoothing system are adjusted.

In an alternative embodiment, triggering events or parameter adjustment events occur at selected times within a time interval. For example, monitoring for the triggering event or parameter adjustment events includes monitoring a time interval, such as the time of the day, week, month, year or event the season of the year. The triggering event or parameter adjustment event is then detected at a first time in the time interval, where the first time is either programmed by the physician or set based on the implantable systems analysis of one or more detected signals. For example, when it is known by the physician or determined by the implantable pulse generator that a patient does not experience tachyarrhythmia during a certain time of the day (e.g., in the hours between 12 midnight and 4 a.m.) the triggering event (to turn the rate smoothing off) or the parameter adjustment event can be programmed as occurring at 12 midnight, with the duration of the first time interval lasting for approximately 4 hours.

In an additional embodiment, the triggering event or parameter adjustment event is when a pacemaker mode is changed. For example, when the pacemaker is switched from one mode of operation (e.g., DDD) to a second mode of operation (DVI) a triggering event or parameter adjustment event is detected. Alternatively, the triggering event or parameter adjustment event is when one or more pacing parameters are changed.

Other triggering events or parameter adjustment events include analyzing one or more cardiac signals to detect the occurrence of an arrhythmic episode. In one embodiment, the arrhythmic episodes can include ventricular tachycardias or ventricular bradycardias. Once the arrhythmic episode is treated, an end to the arrhythmic episode is identified. Once the end of the arrhythmic event is identified, the triggering event or parameter adjusting event is declared. The stability of the intervals can also be used as either a triggering event or a parameter adjusting event. In one embodiment, a stability analysis measures the consistency, or variability, of intervals for the sensed; contractions. For example, as a cardiac signal is sensed the consistency of the sensed cardiac intervals are analyzed. When the variability in the cycle length intervals exceeds a set value a stability problem is declared. Once declared, the triggering event or the parameter adjusting event is identified. The user can also request that a triggering event or a parameter adjusting event be considered. In this embodiment, the system receives a request for either a triggering event (e.g., to turn on rate smoothing) or a parameter adjustment event (e.g., make changes to the parameters). The system analyzes the cardiac condition and either issues or denies the request to issue the parameter adjusting event or the triggering event based on the analysis of the cardiac condition.

Figure 5:
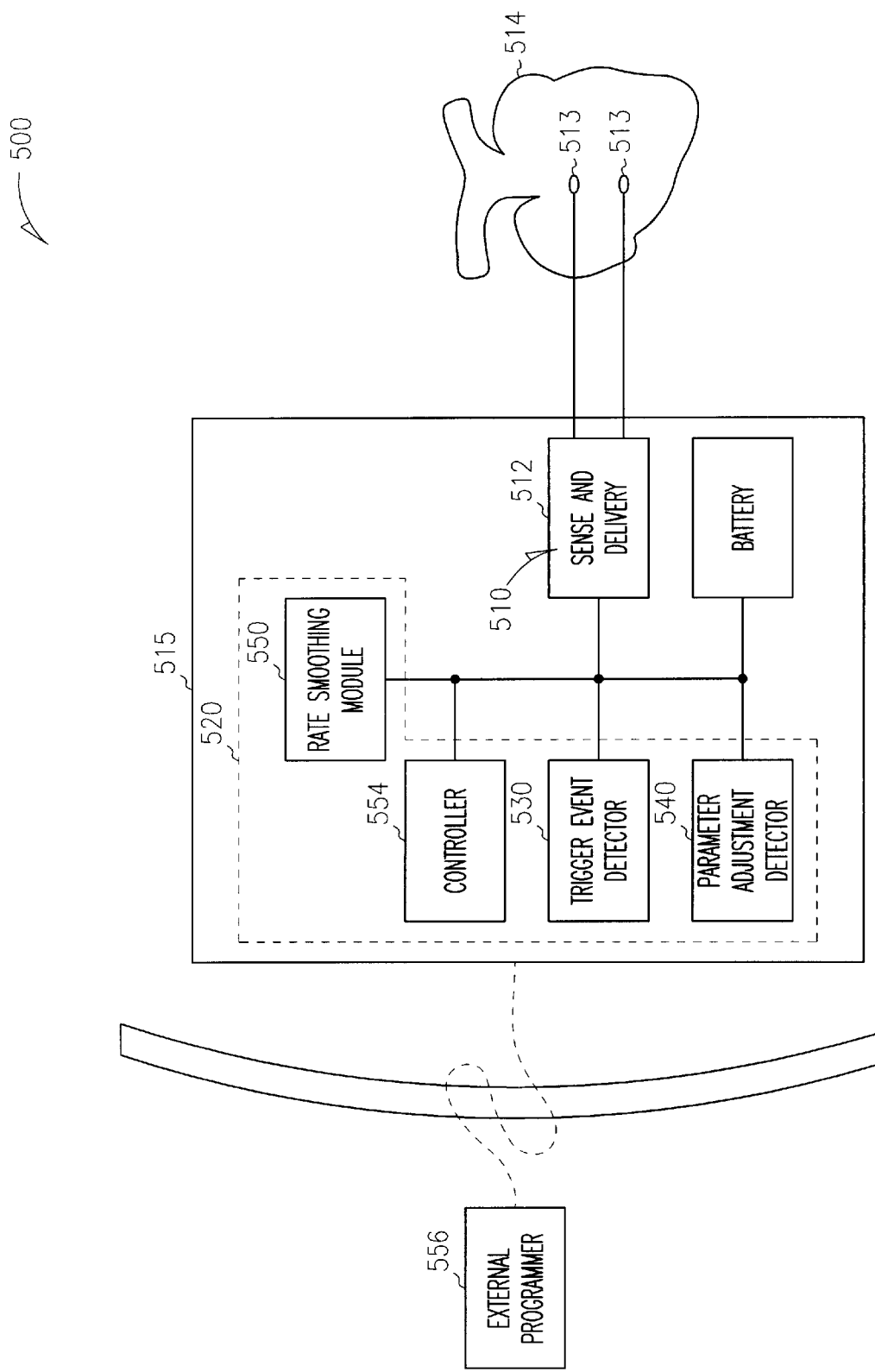
FIG. 5 is a block diagram of one embodiment of an implantable medical device according to the present subject matter.

FIG. 5 shows one embodiment of a system 500 according to the present subject matter. The system includes a signal input system 510, where the signal input system 510 is adapted to monitor a signal. In one embodiment, the signal is any of the signals previously discussed. In the embodiment shown in FIG. 5, the signal input system 510 is a cardiac signal sensing system 512, which includes cardiac electrodes 513 implanted in or on the heart 514 to allow for cardiac signals to be sensed. In one embodiment, the cardiac electrodes 513 are coupled to an implantable pulse generator housing 515, and the control circuitry therein, to allow for either unipolar or bipolar cardiac signals to be sensed from the supraventricular region and/or the ventricular region of the heart 514. Pacing pulses can also be delivered to either the supraventricular and/or ventricular region of the heart through the cardiac electrodes 513 under the control of the cardiac signal sensing system 512 and the control circuitry 520.

The system 500 includes control circuitry 520, where the control circuitry 520 is coupled to the signal input system 510. The control circuitry 520 receives the signal from the signal input system 510, where the signal is processed by the control circuitry 520. The control circuitry 520 includes a trigger event detector 530, where the trigger event detector 530 analyzes the signal to detect a trigger event. The control circuity 520 further includes a parameter adjustment event detector 540, where the parameter adjustment event detector 540 analyzes the signal to detect a parameter adjustment event. The control circuitry 520 further includes a rate smoothing module 550, where the rate smoothing module 550 executes the rate smoothing protocols and makes changes to the rate smoothing parameters once parameter adjustment events are identified. In one embodiment, the components of the control circuity 520 are under the control of a microcontroller 554. The control circuitry 520 also has communication circuity which allows the implantable system 500 to communicate with an external programmer 560.

In one embodiment, the cardiac signal sensing system 512 senses and analyzes a ventricular cardiac signal. The ventricular cardiac signal is then analyzed by the trigger event detector 530 and the parameter adjustment event detector 540 to detect any occurrence of a series of consecutive ventricular intervals having a short-long-short sequence as previously discussed. In addition, the trigger event detector 530 and the parameter adjustment event detector 540 also analyze the ventricular cardiac signal to detect premature ventricular contractions in the ventricular cardiac signal as previously discussed.

FIG. 6 shows an additional embodiment of a system 600 according to the present subject matter. The system 600 includes components similar to those in system 500, but system 600 further includes at least one additional input 610 into the signal input system. In one embodiment, the additional input 610 is a minute ventilation sensor. Signals from the minute ventilation sensor are delivered to both the trigger event detector 530 and the parameter adjustment detector 540. The trigger event detector 530 and the parameter adjustment detector 540 then analyze the signals from the minute ventilation sensor to determine when the signal exceeds a first value, as previously discussed.

In an alternative embodiment, the additional input 610 an accelerometer sensor. Signals from the accelerometer sensor are delivered to both the trigger event detector 530 and the parameter adjustment detector 540. The trigger event detector 530 and the parameter adjustment detector 540 then analyze the signals from the accelerometer sensor to determine when the signal exceeds a first value, as previously discussed.

FIG. 6 also shows the control circuity 520 further including an arrhythmia detection circuit 620. In one embodiment, the arrhythmia detection circuit 620 is coupled to the signal input system 510 and receives and analyzes ventricular cardiac signal to detect an arrhythmic episode, including an end to the arrhythmic episode. The trigger event detector 530 and the parameter adjustment detector 540 then declare events at the end of the arrhythmic episode.

Although specific embodiments have been illustrated and described herein, it will be appreciated by those of ordinary skill in the art that any arrangement which is calculated to achieve the same purpose may be substituted for the specific embodiment shown. This application is intended to cover any adaptations or variations of the present invention. Therefore, it is intended that this invention be limited only by the claims and the equivalents thereof.

What is claimed is:

1. A system, comprising:
    a signal input system including a cardiac signal sensing system adapted to monitor a ventricular signal; and
    control circuitry coupled to the signal input system, the control circuitry receiving the ventricular signal from the signal input system and including:
        a trigger event detector adapted to detect a trigger event in the ventricular signal, the trigger event being a series of consecutive ventricular intervals having a short-long-short sequence; and
        a rate smoothing module activated to provide rate smoothing when the trigger event is detected.

2. the system of claim 1 wherein the rate smoothing module is activated for a programmable time interval after detection of a triggering event.

3. The system of claim 1 wherein the rate smoothing module is activated upon detection of a triggering event and remains active until a triggering event is no longer detected.

4. The system of claim 1 wherein the rate smoothing module, if activated, is deactivated at a programmable time of day.

5. The system of claim 1 further comprising a parameter adjustment event detector for adjusting a parameter of the rate smoothing module when a parameter adjustment event is detected.

6. The system of claim 5 further comprising an activity sensor and wherein a parameter adjustment event is detected when an activity level measured by the activity sensor exceeds a threshold value.

7. The system of claim 6 wherein the activity sensor is a minute ventilation sensor.

8. The system of claim 7 wherein the activity sensor is an accelerometer.

9. The system of claim 5 wherein a parameter adjustment event is detected when a measured heart rate exceeds a threshold value.

10. The system of claim 5 wherein a parameter adjustment event is detected when a PVC occurs.

11. A system, comprising:
    a signal input system including a cardiac signal sensing system adapted to monitor a ventricular signal; and
    control circuitry coupled to the signal input system, the control circuitry receiving the ventricular signal from the signal input system and including:
        a parameter adjustment event detector adapted to detect a parameter adjustment event in the ventricular signal, the parameter adjustment event being a series of consecutive ventricular intervals having a short-long-short sequence; and
        a rate smoothing module including a rate smoothing parameter and adjusting the rate smoothing parameter when the parameter adjustment event is detected.

12. The system of claim 11 wherein the rate smoothing parameter is adjusted for a programmable time interval after detection of a parameter adjustment event.

13. The system of claim 11 wherein the rate smoothing parameter is adjusted upon detection of a parameter adjustment event and remains adjusted until a parameter adjustment event is no longer detected.

14. The system of claim 11 further comprising a trigger event detector for activating the rate smoothing module when a trigger event is detected.

15. The system of claim 14 further comprising an activity sensor and wherein a trigger event is detected when an activity level measured by the activity sensor exceeds a threshold value.

16. The system of claim 15 wherein the activity sensor is a minute ventilation sensor.

17. The system of claim 15 wherein the activity sensor is an accelerometer.

18. The system of claim 14 wherein a trigger event is detected when a measured heart rate exceeds a threshold value.

19. The system of claim 14 wherein a trigger event is detected when a PVC occurs.

* * * * *

UNITED STATES PATENT AND TRADEMARK OFFICE
CERTIFICATE OF CORRECTION

PATENT NO.    : 6,501,987 B1
DATED         : December 31, 2002
INVENTOR(S)   : Eric G. Lovett and Surekha Palreddy It is certified that error appears in the above-identified patent and that said Letters Patent is hereby corrected as shown below:

<u>Column 9,</u>
Line 37, delete "the" and insert -- The -- therefor.

Signed and Sealed this

Thirtieth Day of September, 2003

JAMES E. ROGAN
*Director of the United States Patent and Trademark Office*